(12) United States Patent
Pletz et al.

(10) Patent No.: US 8,788,281 B1
(45) Date of Patent: Jul. 22, 2014

(54) SYSTEM AND METHOD FOR PROCESSING QUALIFIED HEALTHCARE ACCOUNT RELATED FINANCIAL TRANSACTIONS

(75) Inventors: Tracy Pletz, Wilmington, DE (US); Joseph Rochford, West Chester, PA (US)

(73) Assignee: JP Morgan Chase Bank, N.A., New York, NY (US)

( * ) Notice: Subject to any disclaimer, the term of this patent is extended or adjusted under 35 U.S.C. 154(b) by 682 days.

(21) Appl. No.: 12/115,850

(22) Filed: May 6, 2008

Related U.S. Application Data (60) Provisional application No. 60/991,920, filed on Dec. 3, 2007.

(51) Int. Cl.
*G06Q 50/00* (2012.01)
*G06Q 10/00* (2012.01)

(52) U.S. Cl.
USPC .................................. 705/2; 705/3

(58) Field of Classification Search
USPC ............................................. 705/2
See application file for complete search history.

(56) References Cited

U.S. PATENT DOCUMENTS

| | | | |
|---|---|---|---|
| 3,653,480 A | 4/1972 | Yamamoto et al. | |
| 4,205,780 A | 6/1980 | Burns et al. | |
| 4,321,672 A | 3/1982 | Braun et al. | |
| 4,396,985 A | 8/1983 | Ohara et al. | |
| 4,491,725 A * | 1/1985 | Pritchard | 705/2 |
| 4,495,018 A | 1/1985 | Vohrer et al. | |
| 4,617,457 A | 10/1986 | Granzow et al. | |
| 4,672,377 A | 6/1987 | Murphy et al. | |
| 4,700,055 A | 10/1987 | Kashkashian, Jr. | |
| 4,752,877 A | 6/1988 | Roberts et al. | |
| 4,797,913 A | 1/1989 | Kaplan et al. | |
| 4,799,156 A | 1/1989 | Shavit et al. | |
| 4,812,628 A | 3/1989 | Boston et al. | |
| 4,823,264 A | 4/1989 | Deming | |
| 4,931,793 A | 6/1990 | Fuhrmann et al. | |
| 4,948,174 A | 8/1990 | Thomson et al. | |
| 4,974,878 A | 12/1990 | Josephson | |
| 4,988,849 A | 1/1991 | Sasaki et al. | |
| 4,992,646 A | 2/1991 | Collin et al. | |
| 5,023,904 A | 6/1991 | Kaplan et al. | |
| 5,053,607 A | 10/1991 | Carlson et al. | |
| 5,054,096 A | 10/1991 | Beizer | |
| 5,080,748 A | 1/1992 | Bonomi | |
| 5,111,395 A | 5/1992 | Smith et al. | |
| 5,121,945 A | 6/1992 | Thomson et al. | |
| 5,122,950 A | 6/1992 | Benton et al. | |
| 5,136,502 A | 8/1992 | Van Remortel et al. | |
| 5,175,682 A | 12/1992 | Higashiyama et al. | |
| 5,198,975 A | 3/1993 | Baker et al. | |
| 5,220,501 A | 6/1993 | Lawlor et al. | |
| 5,225,978 A | 7/1993 | Petersen et al. | |
| 5,237,159 A | 8/1993 | Stephens et al. | |

(Continued)

OTHER PUBLICATIONS

Thorpe, Medical Savings Accounts: Design and Policy Issues, Health Affairs, 14, No. 3 (1995):254-259.*

*Primary Examiner* — Tran Nguyen
(74) *Attorney, Agent, or Firm* — Goodwin Procter, LLP (57) ABSTRACT

This invention relates to a system and method for processing qualified healthcare account transactions (e.g., HFA, Health FSA, and HRA) and non-qualified credit card transactions within a transaction processing system. In particular, this invention relates to a multi-purse payment device associated with a transaction processing system for auto-substantiating qualified healthcare transactions.

58 Claims, 3 Drawing Sheets

(56) References Cited

U.S. PATENT DOCUMENTS

| | | | |
|---|---|---|---|
| 5,283,829 A | 2/1994 | Anderson |
| 5,287,269 A | 2/1994 | Dorrough et al. |
| 5,311,594 A | 5/1994 | Penzias |
| 5,315,508 A | 5/1994 | Bain et al. |
| 5,321,238 A | 6/1994 | Kamata et al. |
| 5,326,959 A | 7/1994 | Perazza |
| 5,336,870 A | 8/1994 | Hughes et al. |
| 5,350,906 A | 9/1994 | Brody et al. |
| 5,367,581 A | 11/1994 | Abel et al. |
| 5,373,550 A | 12/1994 | Campbell et al. |
| 5,396,417 A | 3/1995 | Burks et al. |
| 5,402,474 A | 3/1995 | Miller et al. |
| 5,412,190 A | 5/1995 | Josephson et al. |
| 5,424,938 A | 6/1995 | Wagner et al. |
| 5,430,644 A | 7/1995 | Deaton et al. |
| 5,432,506 A | 7/1995 | Chapman |
| 5,444,794 A | 8/1995 | Uhland, Sr. |
| 5,444,841 A | 8/1995 | Glaser et al. |
| 5,446,740 A | 8/1995 | Yien et al. |
| 5,448,471 A | 9/1995 | Deaton et al. |
| 5,465,206 A | 11/1995 | Hilt et al. |
| 5,477,040 A | 12/1995 | Lalonde |
| 5,479,494 A | 12/1995 | Clitherow |
| 5,483,445 A | 1/1996 | Pickering |
| 5,484,988 A | 1/1996 | Hills et al. |
| 5,502,576 A | 3/1996 | Ramsay et al. |
| 5,504,677 A | 4/1996 | Pollin |
| 5,506,691 A | 4/1996 | Bednar et al. |
| 5,513,250 A | 4/1996 | McAllister |
| 5,532,464 A | 7/1996 | Josephson et al. |
| 5,544,046 A | 8/1996 | Niwa et al. |
| 5,550,734 A | 8/1996 | Tarter et al. |
| 5,551,021 A | 8/1996 | Harada et al. |
| 5,557,515 A | 9/1996 | Abbruzzese et al. |
| 5,563,400 A | 10/1996 | Le Roux et al. |
| 5,566,330 A | 10/1996 | Sheffield |
| 5,568,489 A | 10/1996 | Yien et al. |
| 5,570,465 A | 10/1996 | Tsakanikas |
| 5,572,004 A | 11/1996 | Raimann et al. |
| 5,575,515 A | 11/1996 | Iwamoto et al. |
| 5,583,759 A | 12/1996 | Geer |
| 5,583,760 A | 12/1996 | Klesse |
| 5,590,196 A | 12/1996 | Moreau et al. |
| 5,590,197 A | 12/1996 | Chen et al. |
| 5,592,377 A | 1/1997 | Lipkin |
| 5,592,378 A | 1/1997 | Cameron et al. |
| 5,599,528 A | 2/1997 | Igaki et al. |
| 5,603,025 A | 2/1997 | Tabb et al. |
| 5,615,109 A | 3/1997 | Eder |
| 5,621,201 A | 4/1997 | Langhans et al. |
| 5,640,577 A | 6/1997 | Scharmer |
| 5,642,419 A | 6/1997 | Rosen |
| 5,649,117 A | 7/1997 | Landry |
| 5,652,786 A | 7/1997 | Rogers |
| 5,659,165 A | 8/1997 | Jennings et al. |
| 5,659,469 A | 8/1997 | Deaton et al. |
| 5,659,741 A | 8/1997 | Eberhardt |
| 5,666,493 A | 9/1997 | Wojcik et al. |
| 5,677,955 A | 10/1997 | Doggett et al. |
| 5,679,938 A | 10/1997 | Templeton et al. |
| 5,679,940 A | 10/1997 | Templeton et al. |
| 5,692,132 A | 11/1997 | Hogan |
| 5,699,528 A | 12/1997 | Hogan |
| 5,703,344 A | 12/1997 | Bezy et al. |
| 5,704,044 A | 12/1997 | Tarter et al. |
| 5,708,422 A | 1/1998 | Blonder et al. |
| 5,715,298 A | 2/1998 | Rogers |
| 5,715,314 A | 2/1998 | Payne et al. |
| 5,715,399 A | 2/1998 | Bezos |
| 5,717,989 A | 2/1998 | Tozzoli et al. |
| 5,724,424 A | 3/1998 | Gifford |
| 5,727,249 A | 3/1998 | Pollin |
| 5,748,780 A | 5/1998 | Stolfo |
| 5,751,842 A | 5/1998 | Riach et al. |
| 5,757,917 A | 5/1998 | Rose et al. |
| 5,770,843 A | 6/1998 | Rose et al. |
| 5,774,553 A | 6/1998 | Rosen |
| 5,784,696 A | 7/1998 | Melnikoff |
| 5,793,861 A | 8/1998 | Haigh |
| 5,794,221 A | 8/1998 | Egendorf |
| 5,802,498 A | 9/1998 | Comesanas |
| 5,802,499 A | 9/1998 | Sampson et al. |
| 5,819,236 A | 10/1998 | Josephson |
| 5,819,238 A | 10/1998 | Fernholz |
| 5,826,241 A | 10/1998 | Stein et al. |
| 5,826,245 A | 10/1998 | Sandberg-Diment |
| 5,832,447 A | 11/1998 | Rieker et al. |
| 5,832,460 A | 11/1998 | Bednar et al. |
| 5,832,463 A | 11/1998 | Funk |
| 5,832,464 A | 11/1998 | Houvener et al. |
| 5,832,488 A | 11/1998 | Eberhardt |
| 5,835,580 A | 11/1998 | Fraser |
| 5,835,603 A | 11/1998 | Coutts et al. |
| 5,835,899 A | 11/1998 | Rose et al. |
| 5,852,812 A | 12/1998 | Reeder |
| 5,859,419 A | 1/1999 | Wynn |
| 5,859,779 A * | 1/1999 | Giordano et al. ............ 700/231 |
| 5,864,609 A | 1/1999 | Cross et al. |
| 5,870,456 A | 2/1999 | Rogers |
| 5,870,721 A | 2/1999 | Norris |
| 5,870,723 A | 2/1999 | Pare, Jr. et al. |
| 5,870,725 A | 2/1999 | Bellinger et al. |
| 5,873,072 A | 2/1999 | Kight et al. |
| 5,883,810 A | 3/1999 | Franklin et al. |
| 5,884,288 A | 3/1999 | Chang et al. |
| 5,897,625 A | 4/1999 | Gustin et al. |
| 5,898,157 A | 4/1999 | Mangili et al. |
| 5,903,881 A | 5/1999 | Schrader et al. |
| 5,910,896 A | 6/1999 | Hahn-Carlson |
| 5,910,988 A | 6/1999 | Ballard |
| 5,917,965 A | 6/1999 | Cahill et al. |
| 5,920,847 A | 7/1999 | Kolling et al. |
| 5,930,778 A | 7/1999 | Geer |
| 5,940,811 A | 8/1999 | Norris |
| 5,940,844 A | 8/1999 | Cahill et al. |
| 5,943,656 A | 8/1999 | Crooks et al. |
| 5,945,653 A | 8/1999 | Walker et al. |
| 5,956,700 A | 9/1999 | Landry |
| 5,963,659 A | 10/1999 | Cahill et al. |
| 5,963,925 A | 10/1999 | Kolling et al. |
| 5,966,698 A | 10/1999 | Pollin |
| 5,978,780 A | 11/1999 | Watson |
| 5,987,435 A | 11/1999 | Weiss et al. |
| 5,987,436 A | 11/1999 | Halbrook |
| 5,987,439 A | 11/1999 | Gustin et al. |
| 5,991,750 A | 11/1999 | Watson |
| 6,000,832 A | 12/1999 | Franklin et al. |
| 6,003,762 A | 12/1999 | Hayashida |
| 6,006,208 A | 12/1999 | Forst et al. |
| 6,009,442 A | 12/1999 | Chen et al. |
| 6,014,636 A | 1/2000 | Reeder |
| 6,016,482 A | 1/2000 | Molinari et al. |
| 6,032,133 A | 2/2000 | Hilt et al. |
| 6,032,137 A | 2/2000 | Ballard |
| 6,035,281 A | 3/2000 | Crosskey et al. |
| 6,035,285 A | 3/2000 | Schlect et al. |
| 6,035,287 A | 3/2000 | Stallaert et al. |
| 6,038,553 A | 3/2000 | Hyde, Jr. |
| 6,041,312 A | 3/2000 | Bickerton et al. |
| 6,041,315 A | 3/2000 | Pollin |
| 6,044,362 A | 3/2000 | Neely |
| 6,052,674 A | 4/2000 | Zervides et al. |
| 6,058,380 A | 5/2000 | Anderson et al. |
| 6,058,381 A | 5/2000 | Nelson et al. |
| 6,061,665 A | 5/2000 | Bahreman |
| 6,065,675 A | 5/2000 | Teicher et al. |
| 6,067,524 A | 5/2000 | Byerly et al. |
| 6,070,150 A | 5/2000 | Remington et al. |
| 6,070,798 A | 6/2000 | Nethery |
| 6,073,104 A | 6/2000 | Field |
| 6,073,113 A | 6/2000 | Guinan |
| 6,076,072 A | 6/2000 | Libman |
| 6,078,907 A | 6/2000 | Lamm |
| 6,081,790 A | 6/2000 | Rosen |

(56) References Cited

U.S. PATENT DOCUMENTS

| | | | |
|---|---|---|---|
| 6,085,168 A | 7/2000 | Mori et al. | |
| 6,088,683 A | 7/2000 | Jalili | |
| 6,088,685 A | 7/2000 | Kiron et al. | |
| 6,088,686 A | 7/2000 | Walker et al. | |
| 6,092,056 A | 7/2000 | Tull, Jr. et al. | |
| 6,098,053 A | 8/2000 | Slater | |
| 6,098,070 A | 8/2000 | Maxwell | |
| 6,105,011 A | 8/2000 | Morrison, Jr. | |
| 6,108,639 A | 8/2000 | Walker et al. | |
| 6,108,641 A * | 8/2000 | Kenna et al. | 705/35 |
| 6,110,044 A | 8/2000 | Stern | |
| 6,111,858 A | 8/2000 | Greaves et al. | |
| 6,115,690 A | 9/2000 | Wong | |
| 6,119,106 A | 9/2000 | Mersky et al. | |
| 6,119,107 A | 9/2000 | Polk | |
| 6,125,354 A | 9/2000 | MacFarlane et al. | |
| 6,128,602 A | 10/2000 | Northington et al. | |
| 6,128,603 A | 10/2000 | Dent et al. | |
| 6,129,273 A | 10/2000 | Shah | |
| 6,138,118 A | 10/2000 | Koppstein et al. | |
| 6,144,946 A | 11/2000 | Iwamura et al. | |
| 6,148,293 A | 11/2000 | King | |
| 6,149,056 A | 11/2000 | Stinson et al. | |
| 6,181,837 B1 | 1/2001 | Cahill et al. | |
| 6,185,544 B1 | 2/2001 | Sakamoto et al. | |
| 6,202,054 B1 | 3/2001 | Lawlor et al. | |
| 6,205,433 B1 | 3/2001 | Boesch et al. | |
| 6,227,447 B1 | 5/2001 | Campisano | |
| 6,233,566 B1 | 5/2001 | Levine et al. | |
| 6,236,972 B1 | 5/2001 | Shkedy | |
| 6,240,444 B1 | 5/2001 | Fin et al. | |
| 6,278,981 B1 | 8/2001 | Dembo et al. | |
| 6,289,322 B1 | 9/2001 | Kitchen et al. | |
| 6,301,379 B1 | 10/2001 | Thompson et al. | |
| 6,304,858 B1 | 10/2001 | Mosler et al. | |
| 6,321,212 B1 | 11/2001 | Lange | |
| 6,338,047 B1 | 1/2002 | Wallman | |
| 6,338,049 B1 | 1/2002 | Walker et al. | |
| 6,374,235 B1 | 4/2002 | Chen et al. | |
| 6,393,409 B2 | 5/2002 | Young et al. | |
| 6,405,173 B1 | 6/2002 | Honarvar et al. | |
| 6,408,284 B1 * | 6/2002 | Hilt et al. | 705/40 |
| 6,415,259 B1 | 7/2002 | Wolfinger et al. | |
| 6,418,419 B1 | 7/2002 | Nieboer et al. | |
| 6,418,420 B1 | 7/2002 | DiGiorgio et al. | |
| 6,418,430 B1 | 7/2002 | DeFazio et al. | |
| 6,490,568 B1 | 12/2002 | O'Mara et al. | |
| 6,493,685 B1 | 12/2002 | Ensel et al. | |
| 6,574,377 B1 | 6/2003 | Cahill et al. | |
| 6,578,015 B1 | 6/2003 | Haseltine et al. | |
| 6,609,113 B1 | 8/2003 | O'Leary et al. | |
| 6,609,125 B1 | 8/2003 | Layne et al. | |
| 6,629,081 B1 | 9/2003 | Cornelius et al. | |
| 6,704,714 B1 | 3/2004 | O'Leary et al. | |
| 6,721,715 B2 | 4/2004 | Nemzow | |
| 7,380,707 B1 | 6/2008 | Fredman | |
| 2001/0018739 A1 | 8/2001 | Anderson et al. | |
| 2001/0037309 A1 | 11/2001 | Vrain | |
| 2001/0047334 A1 | 11/2001 | Nappe et al. | |
| 2001/0047489 A1 | 11/2001 | Ito et al. | |
| 2002/0012445 A1 | 1/2002 | Perry | |
| 2002/0013728 A1 | 1/2002 | Wilkman | |
| 2002/0026394 A1 | 2/2002 | Savage et al. | |
| 2002/0038363 A1 | 3/2002 | MacLean | |
| 2002/0052842 A1 | 5/2002 | Schuba et al. | |
| 2002/0069134 A1 | 6/2002 | Solomon | |
| 2002/0077978 A1 | 6/2002 | O'Leary et al. | |
| 2002/0087468 A1 | 7/2002 | Ganesan et al. | |
| 2002/0091635 A1 | 7/2002 | Dilip et al. | |
| 2002/0107770 A1 | 8/2002 | Meyer et al. | |
| 2002/0107788 A1 | 8/2002 | Cunningham | |
| 2002/0111837 A1 | 8/2002 | Aupperle | |
| 2002/0138398 A1 | 9/2002 | Kalin et al. | |
| 2002/0170966 A1 | 11/2002 | Hannigan et al. | |
| 2002/0178071 A1 | 11/2002 | Walker et al. | |
| 2002/0194096 A1 | 12/2002 | Falcone et al. | |
| 2002/0198817 A1 | 12/2002 | Dhir | |
| 2002/0199182 A1 | 12/2002 | Whitehead | |
| 2003/0018557 A1 | 1/2003 | Gilbert et al. | |
| 2003/0046218 A1 | 3/2003 | Albanese et al. | |
| 2003/0097335 A1 | 5/2003 | Moskowitz et al. | |
| 2003/0105641 A1 | 6/2003 | Lewis | |
| 2003/0208421 A1 | 11/2003 | Vicknair et al. | |
| 2003/0208441 A1 | 11/2003 | Poplawski et al. | |
| 2003/0225663 A1 | 12/2003 | Horan et al. | |
| 2003/0233305 A1 | 12/2003 | Solomon | |
| 2004/0078328 A1 | 4/2004 | Talbert et al. | |
| 2005/0033690 A1 | 2/2005 | Antognini et al. | |
| 2006/0106650 A1 | 5/2006 | Bush | |

* cited by examiner

SYSTEM AND METHOD FOR PROCESSING QUALIFIED HEALTHCARE ACCOUNT RELATED FINANCIAL TRANSACTIONS

CROSS-REFERENCE TO RELATED APPLICATIONS

The present application claims priority to U.S. Provisional Patent Application No. 60/991,920, filed Dec. 3, 2007, which is hereby incorporated by reference herein in its entirety.

FIELD OF THE INVENTION

This invention relates to a system and method for processing qualified healthcare debit card transactions and non-qualified credit card transactions within a transaction processing system. In particular, this invention relates to a multi-purse payment device associated with a transaction processing system for auto-substantiating qualified healthcare transactions.

BACKGROUND OF THE INVENTION

Consumer-directed accounts are dedicated funding pools used for health care expenses at the discretion of an individual. These accounts can be procured either individually or through an employer, and may or may not involve tax advantages to the user of the account. A key requirement in the use of consumer-directed accounts is that they finance only those goods and services that are authorized by the Internal Revenue Service ("IRS") as eligible medical expenses.

The IRS limitations create the need for close oversight of consumer-directed account programs, which involves high paper volumes, manual intervention, and substantial administrative expense to ensure compliance. In addition, the current process often requires participants to pay for goods and services and then file for reimbursement out of the funds contributed to the consumer-directed account. This requires participants to make the payment up-front (even though the funds may have already been set aside) and to handle a variety of paper documents during filing and reimbursement.

These challenges significantly undermine the efficiency of consumer-directed account programs, resulting in dissatisfied participants and program sponsors. Given these difficulties, there is a clear need for an electronic solution that automates the use of consumer-directed accounts, while maintaining compliance with the rules and regulations under which consumer-directed accounts are governed.

The trend to consumer-directed health care has been supported by three major legislative innovations within the past thirty years; namely, the Revenue Act of 1978, the Health Insurance Portability and Accountability Act of 1996 (HIPAA) and a ruling in 2002 by the IRS establishing Health Reimbursement Arrangements. Each of these initiatives created the model for a consumer-directed account in use today. The Revenue Act of 1978 created Flexible Spending Accounts (FSAs), which are employer-sponsored accounts funded by employees' pre-tax contributions from payroll.

FSAs can be established and used for a variety of purposes, such as the payment of health care, dependent care, or public transportation expenses. The IRS Code determines what types of health care expenses qualify for reimbursement from an FSA. For example, some reimbursable expenses include: co-payments and deductibles for health care expenses, vision expenses, ambulance expenses, oxygen equipment, wheelchairs, prescription drugs, and the like.

Because FSAs are funded with pre-tax dollars, participants in an FSA program can realize substantial savings on eligible expenses. Employers value FSA programs because these accounts provide benefits to employees and reduce employees' taxable income on which an employer must pay Federal Insurance Contributions Act (FICA) taxes.

Currently, there are more than 8 million Health FSAs in the United States, with over 9 billion dollars in annual contributions. Health FSA contributions are expected to grow significantly over the next several years, as consumers take on more of the burden for health care costs and seek tax-advantaged tools to finance those expenses.

Two other types of consumer-directed accounts—the Medical Savings Account (MSA) and the Health Reimbursement Arrangement (HRA)—were introduced within the past decade. The MSA was established with the passage of HIPAA in 1996. The MSA provides for a tax-advantaged account reserved for individuals who are self-employed or employed at a small business, and who use a qualifying high-deductible health plan. The MSA is designed to provide tax benefits on payments towards a deductible portion of the high-deductible health plan. A key advantage of the MSA to participants is the ability to carry over unused funds in the account from one plan year to the next. This differs from FSA programs that require unused funds to be forfeited by the employee and turned over to the employer health plan, a requirement commonly known as the FSA "use it or lose it" provision. The IRS established the HRA in June 2002, drawing on the strengths of both the FSA and the MSA. For example, employers of all sizes may implement an HRA program (e.g., FSA). In addition, unused funds contributed to an HRA may roll over from one plan year to the next, like MSA. Due to its flexibility and attractiveness to employees, the HRA is expected to quickly become prevalent throughout the employee benefits marketplace.

A result of these initiatives is the proliferation of consumer-directed accounts used to provide tax advantages for health care spending. Although FSA, MSA, and HRA are the most common forms of consumer-directed accounts, others may also exist. As consumer-directed health care evolves, there will be continued innovation in the field of consumer-directed accounts. This will likely result in new account structures being introduced over time.

Most consumer-directed accounts offered through an employer benefits plan are managed and administered by an entity other than the employer itself, usually a Third Party Administrator (TPA). A TPA can provide a variety of services to employers, such as managing claim submissions from employees and generating reports on plan usage. The requirements to comply with IRS guidelines for expense eligibility create a heavy burden on the TPA in managing a consumer-directed account program.

Typically, the employee participant, i.e. FSA account holder, designates a portion of his or her compensation into an FSA on a tax-free basis. The employee receives desired goods and services of which the employee's health insurance may pay for a portion or all of the cost.

The employee may be issued a debit card for withdrawals from their FSA. In recent years, the FSA debit card was developed to eliminate "double-dipping" by allowing employees to access the FSA directly, as well as to simplify the substantiation requirement which required labor-intensive claims processing; the debit card also enhances the effect of "pre-funding" medical FSAs. However, the substantiation requirement itself did not go away, and has even been expanded on by the IRS for the debit-card environment; therefore, withdrawal issues still remain for FSAs.

According to Celent, as of May 2006, there were approximately 6 million debit cards in the market tied to an FSA account, representing 25% of the FSA participating community. Celent projects that FSA cards will increase FSA adoption rates. The average card participation rate was around 20% as of May 2006. By 2010, it is projected this rate will increase to 85%.

Typically, such cards are not accepted by all merchants that accept debit and credit cards, but only by those merchants that accept FSA debit cards. Merchant codes and product codes are used at the point of sale to restrict sales if the products are not eligible healthcare related purchases. In the occasional instance that a qualifying purchase is rejected, another form of payment must be used (a check or payment from another account).

In the case of pharmacy transactions, for example, a pharmacy benefits manager ("PBM") determines of the amount an employee's health insurer will pay. Often, the employee is required to pay at least a percentage or flat fee. If the out-of-pocket employee payment is a qualified expense under the IRS Code, the employee may present an FSA debit card to complete the purchase, or tender a different payment method, and thereafter complete and submit a claim form to an TPA. Upon approval and processing, the proper amount is deducted from the employee's consumer healthcare account and a reimbursement check is sent to the employee.

Whenever an employee files for reimbursement out of a consumer-directed account, the TPA must audit and validate the claim to ensure that it is for a valid medical expense. Typically, an employee will provide proof of eligibility in the form of a paper receipt or invoice documenting the nature of the expense, which the TPA reviews to confirm compliance. This validation process is extremely labor-intensive and generally requires TPA personnel to review a given claim manually. Further complicating the TPA's task of ensuring compliance is the ability of employers to customize expense eligibility rules to their particular program. That is, although the IRS governs what is potentially allowed, employers have the option to limit further the specific types of expenses that their particular consumer-directed account program will authorize. A TPA must therefore consult the plan rules for a given program before granting approval to an employee's claim. After the claim has been deemed eligible and sufficient funds have been confirmed within the employee's consumer-directed account, the TPA will remit funds, usually by paper check, with a paper explanation of payment to the employee.

Because of the challenges associated with the current manual use, processing, and administration of consumer-directed accounts, industry participants have attempted to develop a variety of mechanisms to streamline activities and improve automation. As consumer-directed accounts grow in importance and usage, these efforts will become increasingly relevant to the ways in which health care expenses are paid and managed.

Efforts to innovate within the administration of consumer-directed accounts have focused on the goal of reducing the number of paper claim forms submitted by participants. Manual mechanisms for obviating claim form submission have existed for several years. For example, in some cases, a TPA may be able to make a direct payment from a consumer-directed account to a provider of eligible goods or services without the participant having to file a claim form or initiate a payment. This method is usually applied for payments that are recurring in nature (such as elder care or regular prescription drug purchases), because it requires notifying the provider to change their process and forward an invoice for payment to the TPA directly rather than to the employee. In addition, such payments are only possible when payment is not required at the time services are rendered. For prescription drug transactions within a pharmacy, for example, payment is expected at the point of sale, precluding a post-hoc payment from the TPA to the provider. Moreover, although the participant does not have to file a paper claim form, the TPA must still employ a manual process for adjudicating and paying claims.

Another manual mechanism for reducing the number of paper claim submissions by savings account participants is to automatically apply consumer-directed account funds towards deductibles or co-payments determined under an employer-sponsored health plan. This option has historically been possible only when the TPA manages claims for both the consumer-directed account and the health plan for a given employer. In this scenario, an employee obtains goods or services from a medical provider, causing the provider to generate and submit a claim to the employee's health plan. Once the TPA has adjudicated the claim and determined the employee's payment responsibility, the TPA remits funds from the consumer-directed account directly to the provider, eliminating the need for the employee to pay the provider up-front and then prepare and file a claim with the TPA for reimbursement from the consumer-directed account. However, instances when an individual TPA manages both the consumer-directed accounts and the health plan for a given employer are limited, making this option available to relatively few consumer-directed account participants.

An alternative mechanism for reducing paper claims submissions and improving efficiencies involves enabling electronic claim submission and payment through the use of a stored value program. A stored value program typically includes supplying each participant with a payment card that is linked to a consumer-directed account. A participant then presents the physical card or the card number for payment wherever medical expenses are incurred. The health care provider initiates a payment transaction that transfers funds from the consumer-directed account to the provider's bank account, eliminating the need for the participant to provide up-front payment and then file for later reimbursement through the TPA. Likewise, the TPA benefits by not having to manage and process paper forms and claims associated with the card-initiated transaction. Because of the wide acceptance of payment cards, participants are able to use consumer-directed account funds in a variety of venues, such as in a retail location, through the mail, or over the phone, etc.

In stored value arrangements, payments are made directly from the FSA without being substantiated first as eligible expenses. This forces the TPA to solicit receipts from the employee and make restitution to the FSA for non-compliant claims. Often, the employee is lax with submission and sometimes may fail to submit receipts at all.

Although stored value programs have the potential to create substantial efficiencies and benefits, they also have the potential for substantial abuse. In particular, current programs risk exposing employers and TPAs to non-compliance with IRS guidelines for consumer-directed account expense eligibility. Unlike the manual process that allows a TPA to audit detailed transaction information in the form of a submitted receipt, card transactions generally communicate only the payment amount requested and the type of merchant that is initiating the transaction (e.g., a pharmacy, a toy store, etc.). Many stored value programs thus authorize the use of card payments to merchants that are considered "health care providers" (such as doctors, optometrists, pharmacies, etc.) and deny card transactions at non-health care merchants (such as a toy store or apparel retailer). This type of filtering is inadequate because many putative health care merchants may still sell goods or services that do not meet the IRS guidelines for payment from a consumer-directed account. For example, a consumer-directed account participant receiving services from a physician's office may be receiving cosmetic enhancements that are not medically necessary. Alternatively, a participant may present their card at a pharmacy for payment toward a wide variety of non-eligible goods (e.g., magazines, office supplies, etc.). Unless a stored value program analyzes detailed, individual transaction data to determine expense eligibility, ineligible expenses may be inappropriately authorized and funded by the consumer-directed account.

Accordingly, a system and method for processing qualified healthcare transactions and non-qualified transactions using a single payment system is desirable. Additionally, there is a need for an improved method for processing consumer-directed account transactions which assures that only allowed expenses are reimbursed, alleviates onerous paperwork, and enables customers to purchase both qualified and non-qualified products in a convenient transaction.

SUMMARY OF THE INVENTION

The invention comprises, in one form thereof, a system and method for processing qualified healthcare transactions and non-qualified transactions within a transaction processing system.

In form, the invention includes a computer implemented method for processing consumer account related reimbursement eligible transactions, the computer implemented method comprising the steps of: issuing a user a payment device associated with a credit account and a consumer account; identifying a user transaction made with the payment device at a merchant for one or more purchases; receiving merchant data regarding the user transaction including an authorization request; transmitting a response to the authorization request; identifying reimbursable expenses in the transaction based at least in part on the merchant data; transmitting a reimbursement request to a consumer account administrator for reimbursable expenses; receiving a reimbursement request response from the consumer account administrator; and reimbursing the user for reimbursable expenses based at least in part on the reimbursement request response from the consumer account administrator.

In another form, the invention includes a computer implemented method for processing consumer account related reimbursement eligible transactions, the computer implemented method comprising the steps of: identifying a user transaction initiated at a merchant for one or more purchases with a payment device associated with a credit account and a consumer account; receiving merchant data regarding the user transaction including an authorization request; transmitting an authorization request to a consumer account administrator, wherein the authorization request includes at least some merchant data for identifying reimbursable expenses in the transaction; receiving a response to the authorization request from the consumer account administrator; transmitting an authorization request to a credit account issuer including at least some merchant data identifying non-reimbursable expenses in the transaction; receiving a response to the authorization request from the credit account issuer; and transmitting an authorization response to the merchant including at least in part the response to the authorization request from the consumer account administrator and the response to the authorization request from the credit account issuer.

In yet another form, the invention includes a computer implemented method for processing consumer account related reimbursement eligible transactions, the computer implemented method comprising the steps of: identifying a user transaction initiated at a merchant for one or more purchases with a payment device associated with a credit account and a consumer account; receiving merchant data regarding the user transaction including an authorization request; transmitting an authorization request to a consumer account administrator, wherein the authorization request includes at least some merchant data for identifying reimbursable expenses in the transaction; receiving an authorization response from the consumer account administrator; transmitting the authorization response to the merchant including at least in part the response to the authorization request from the consumer account administrator; receiving merchant data regarding the user transaction including a second authorization request; transmitting merchant data including the second authorization request to a credit account issuer; receiving a response to the second authorization request from the credit account issuer; and transmitting an authorization response to the merchant including at least in part the response to the authorization request from the credit account issuer.

Additionally, the invention includes a system for processing consumer account related reimbursement eligible transactions, the system comprising: a processor for processing a credit transaction for a user's purchase with a payment device associated with a credit account and a consumer account; an eligibility module for identifying consumer account reimbursement eligible expenses in the user's purchase; an authorization request router for routing authorization requests; a credit authorization decision engine for decisioning on authorization requests and generating authorization responses; an authorization response router for routing authorization responses; a reimbursement engine for leveraging data received from the authorization request router to initiate a transaction for reimbursement of eligible expenses in the user's purchase; a reimbursement application engine for applying reimbursement payment amount data; a receipt generation component for generating receipts; and an imaging component for imaging receipts.

The invention also includes a system for processing consumer account related reimbursement eligible transactions, the system comprising: a processor for processing a credit transaction for a user's purchase with a payment device associated with a credit account and a consumer account; a transaction packaging router for routing authorization requests; a routing rules engine for at least one of identifying the user's purchase with a payment device associated with a credit account and a consumer account and applying routing rules; a customer defined criteria rules engine for creating routing rules dependant at least in part upon the user's consumer account enrollment criteria; and a credit authorization decision engine for decisioning on authorization requests and generating authorization responses.

BRIEF DESCRIPTION OF THE DRAWINGS

The present invention is disclosed with reference to the accompanying drawings, wherein.

DETAILED DESCRIPTION

Figure 1:
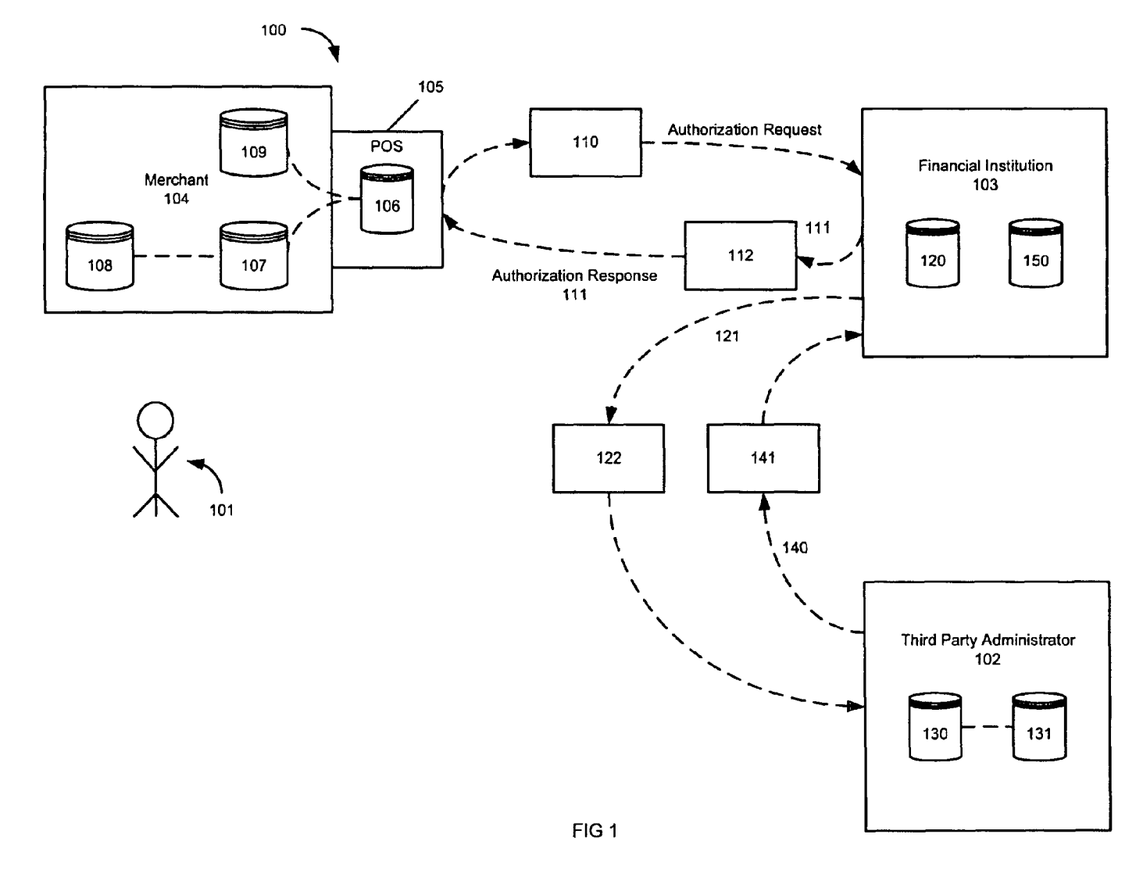
FIG. 1 is a is a block diagram of a system architecture suitable for implementing a single transaction model according to exemplary embodiments of the present invention.

Referring now to FIG. 1, a system architecture suitable for implementing an embodiment of the transaction processing system of the present invention is shown. In system 100, a user 101 (e.g., consumer, participant, employee, etc.) may present a payment device to procure from a merchant 104 both qualified health care goods and services (where reimbursement is available per an established consumer account for eligible medical expenses, such as prescription drugs, doctor's office co-pays, etc.) and non-qualified goods and services. System 100 provides the transaction processing functionality necessary to achieve the user's procurement of qualified and non-qualified goods and services using the payment device. In one embodiment, a multi-purse payment device with a credit lead is associated with system 100. System 100 may be configured to accomplish manual and/or auto-substantiation of healthcare related transactions made with the payment device.

As used herein, the terms "qualified" "eligible," and "allowable" are used interchangeably with respect to goods and services, and refer to those goods and services whose costs are reimbursable at least in part by a consumer account. For example, qualified medical expenses reimbursable by a health FSA may be the same as those medical expenses allowable for the medical tax deduction, as outlined in IRS publication 502.

According to an embodiment of the present invention, a qualified consumer account such as a medical expense FSA (also medical FSA or health FSA) is first made available by an employer and a third party administrator (TPA) 102 to a user 101. A health FSA is similar to a health savings account (HSA) or a health reimbursement account (HRA). However, while HSAs and HRAs are almost exclusively used as components of a consumer driven health care plan, health FSAs are commonly offered with more traditional health plans as well.

For example, HRA and health FSA accounts are typically offered as a benefit by an employer (or an employer's human resources department, or other benefits department or personnel) to an employee, e.g., user 101. The health FSA or HRA programs are then supported by an insurance company, TPA 102, or payroll administrator. In some instances, the employer's particular plan determines how and when funds are available to plan participants (e.g., all funds may be available on the first day of the plan year, or funds may be available only as payroll contributions are made). For health FSAs, an employer or employee will typically contribute pre-tax dollars through payroll deductions. For HRA accounts, funds are generally only contributed by the employer. Both health FSA and HRA accounts require an employer to provide a mechanism for expense substantiation. Generally, neither Health FSA nor HRA account funds can be used by a user to purchase "non-qualified" goods and services.

For HSA accounts, a trustee or custodian financial institution, insurance company, or other IRS-approved entity may offer enrollment. An account may be established by an employer or an individual user, and generally is registered in the user's name. Typically, contributions determine fund availability. HSA accounts, unlike health FSA or HRA accounts, usually require that the user be solely responsible for expense substantiation. Any non-medical expenses procured with accounts funds will be subject to income tax and IRS penalties.

Consumer account registration may be accomplished online, over the phone, through mail, in person or through other forms of communication. Upon registration, system 100, the TPA 102, insurance company, payroll administrator, employer, etc. may associate the user's qualified consumer account with an account number.

During account registration, the user 101 may identify to the account administrator, among other things, a payment mechanism, a funding preference, and a reimbursement preference, e.g., how the user wants payments for qualified health care purchases reimbursed. These preferences are collectively referred to herein as "user enrollment criteria." Routing and processing of transaction data based upon this user enrollment criteria may be accomplished manually or by an automated system. Additionally, the user 101 may direct funds to be reimbursed electronically in a designated account, such as a checking account; credited against an outstanding credit card balance; placed in an investment account to accumulate additional savings over time or other account; or other reimbursement method. Other information and/or preferences may be provided by user 101.

In one embodiment, an FSA debit account is linked to a credit account issued by a financial institution 103. A financial institution may issue the user 101 a Primary Account Number ("PAN") associated with a credit account (e.g., co-brand, private label, etc.). The credit account may then be linked to, for example, an FSA debit account.

The PAN may be associated with any payment device known in the art, including, but not limited to: a credit card, a smart card, RFID card, other funds card, a special device for effecting internet purchases, a program operating on a computer system, a key FOB, a device with a bar code, a phone, a device in a keychain, a processing component in an personal music device and/or any other payment device that is used by a user to effect a transaction. A single PAN may be associated with multiple payment devices for one or more users. Further, the particular payment device may utilize a variety of technologies to interface with a transaction processing system. In one embodiment, a multi-purse payment device is associated with a credit account linked to an FSA debit account.

The PAN or payment device may further be associated with a "rewards" or "points" program sponsored by, for example, the financial institution or other entity. In one embodiment, a user is awarded points, money, goods, services, etc., based upon a volume (e.g., a dollar amount) of purchases made with a payment device associated with the PAN or payment device. In another embodiment, a user is awarded points for purchasing a particular product, making purchases at a particular merchant, etc. Additionally, a user may be rewarded for online bill payment, preauthorized transfers, and or any other account activity. Rewards programs may be structured in any manner known in the art. Typically, the structure of a particular rewards program is determined by the entity underwriting the program. Points or other awards (e.g., certificates) may be redeemed by the user or others for rewards like gift cards, airline tickets, and electronics.

The PAN and/or payment device may also include a "Bank Identification Number" (BIN) or "Issuer Identification Number" (IIN). The BIN may, for example, be the first six digits of a credit card number. These digits may, for example, identify which transaction, payment, and/or association network (e.g., Visa®) the card belongs to, the issuing financial institution, and the nature of the account (i.e., a credit account linked to an FSA debit account). Cards participating in the BIN system may include: credit cards; debit cards; charge cards; stored-value cards; Electronic Benefit Transfer cards, etc. BINs may be also used to indicate the routing mechanism for real time claims. Additionally, online merchants may use BIN lookups to help validate transactions.

The user 101 may register the PAN payment device issued by the financial institution 103 with the TPA 102 and/or system 100. Once the PAN device is registered, the user 101 may use the registered PAN device at a doctor's office, pharmacy and various health care and/or other locations. Purchases may also be made at other merchants who offer eligible as well as ineligible health care products and/or services. Purchases may be made at a merchant store, online, via phone order, mail order or other method of purchasing products and/or services by providing an identifier (e.g., account number, password, PIN, etc.) associated with the user's PAN payment device.

According to one embodiment, the user 101 may present qualified healthcare-related items and/or non-qualified items for purchase at a merchant 104 having a point-of-service ("POS") terminal 105. User 101 may present a PAN payment device, e.g., a multi-purse credit card associated with a credit account linked to an FSA debit account, to purchase the items. The credit card may be swiped/tapped to initiate transaction processing. The merchant's POS terminal 105 reads information stored on the credit card, and software at the POS terminal (e.g., POS processor 106) communicates the credit card information and other financial transaction data to system 100, financial institution 103, or other acquirer via, e.g., a credit card payment gateway, the VISA® Association network, etc.). Communication between the merchant 104, the credit card issuing financial institution 103 may also be accomplished in system 100 over another network, Internet, Ethernet, Intranet, wireless communication and/or other modes of electronic communication or other form of communication.

Financial institution 103 may be separate or combined with system 100. In addition, TPA 102 may be separate or combined with system 100. Other various combinations may be implemented. Further, financial institution 103, TPA 102, and system 100 may all be combined or separate. For example, system 100 may provide consumer account enrollment and user criteria selection services in addition to processing transactions. Additionally, system 100 may be enabled to store user enrollment criteria, transaction data, and reimbursement data in a central database. Such data may further be communicated from system 100 to a financial institution and/or TPA. System 100 may further be accessible by a user to manually upload transaction data not auto-substantiated during transaction processing activities. The system 100 may further be accessible by a user to access and/or download stored transaction data (e.g., purchase receipts). A user may access system 100 by any communication means known in the art, for example, via an internet website. System 100 may further be accessible by a plug-in for computer software, for example, software downloaded or otherwise loaded a user's home computer.

System 100 may practiced with various computer system configurations and may be described in the general context of computer-executable instructions, such as program modules, being executed by a computer. Generally, program modules include routines, programs, objects, components, data structures, etc. that perform particular tasks or implement particular abstract data types. In a distributed computing environment, program modules may be located in both local and remote computer storage media including memory storage devices.

System 100 may include operating systems, application programs, program modules, and program data. The operating systems may be or include a variety of operating systems such as Microsoft Windows® operating system, the Unix operating system, the Linux operating system, the Xenix operating system, the IBM AIX™ operating system, the Hewlett Packard UX™ operating system, the Novell Netware™ operating system, the Sun Microsystems Solaris™ operating system, the OS/2™ operating system, the BeOS™ operating system, the Macintosh™® operating system, the Apache™ operating system, an OpenStep™ operating system or another operating system of platform.

The system of the present invention may further include a memory including at least one set of instructions that is either permanently or temporarily stored. Processors execute the instructions that are stored in order to process data. The set of instructions may include various instructions that perform a particular task or tasks, such as those shown in the appended flowcharts. Such a set of instructions for performing a particular task may be characterized as a program, software program, software, engine, module, component, mechanism, or tool.

The system may also include one or more software processing modules stored in a memory as described above and executed on a processor in the manner described herein. The program modules may be in the form of any suitable programming language, which is converted to machine language or object code to allow the processor or processors to read the instructions. That is, written lines of programming code or source code, in a particular programming language, may be converted to machine language using a compiler, assembler, or interpreter. The machine language may be binary coded machine instructions specific to a particular computer.

Any suitable programming language may be used in accordance with the various embodiments of the invention. Illustratively, the programming language used may include assembly language, Ada, APL, Basic, C, C++, COBOL, dBase, Forth, FORTRAN, Java, Modula-2, Pascal, Prolog, REXX, and/or JavaScript for example. Further, it is not necessary that a single type of instruction or programming language be utilized in conjunction with the operation of the system and method of the invention. Rather, any number of different programming languages may be utilized as is necessary or desirable.

Also, the instructions and/or data used in the practice of the invention may utilize any compression or encryption technique or algorithm, as may be desired. An encryption module might be used to encrypt data. Further, files or other data may be decrypted using a suitable decryption module.

The modules of system 100 may be further combined, duplicated and/or separated. In addition, the modules of system 100 may also be provided across multiple systems and/or other platforms. Other implementations may be realized.

In one embodiment, POS terminal 105 includes an eligibility module 107 for accessing an intermediary database when processing a customer's transaction to obtain line-item data about a purchase. This may be accomplished in real time. The eligibility module 107 may also be deployed on a network in communication with POS 105, or in another location (e.g., in association network infrastructure). Eligibility module 107 may identify qualified expenses and associate product details with transaction data. The databases may also store customer data, payee/recipient data, payment data, etc. Other data may be stored and/or accessed. Other sources of information (e.g., external and/or internal sources of data) may also be accessed by the eligibility module 107.

For example, when processing a purchase, the eligibility module 107 accesses an inventory information approval system ("HAS") to obtain product information. Eligibility module 107 may automatically match purchase activity with the database's information on specific products and services (e.g., medical items defined as "qualified" in an IIAS database 108, or a SKU-level product information database). The eligibility module 107 may also associate purchase activity with data developed for various potential health care transactions using publicly available data sets and/or other sources of data. Data sets may include Prescription drugs (NDC); Dental (CDT); Medical (CPT/ICD-9) and/or Non-prescription medical products (UPC). Other data sets may also be included. As eligible transactions may change in the future, data sets may be modified, added, deleted, etc.

Single Transaction Model

According to an exemplary single transaction model of the present invention, a user presents a multi-purse payment device with a credit lead to a merchant having a POS terminal including POS processor 106. POS processor 106 processes a single authorization credit transaction for the full dollar amount of the purchase. Based on the information matched with the purchase activity by eligibility module 107, a determination may be made as to whether each purchase is eligible for reimbursement or not. For example, the information may include type of product or service, price, purpose, product or service code, date/time of purchase, merchant data, etc. The transaction data is transmitted from the merchant's POS 105 and may be routed to the financial institution 102 or other acquirer for authorization.

In one embodiment, the transaction data is routed via an authorization request router 110, for example, a transaction, payment, and/or association network (e.g., Visa). The authorization request router 110 may match the credit card's BIN to corresponding BINs in a BIN file to recognize that the purchase device relates to a credit account linked with an FSA debit account. The BINs may also be associated with specific routing instructions. In an alternative embodiment, the POS terminal 105 includes an identification module for matching the credit card's BIN to a corresponding BIN in POS BIN file 109. The authorization request router 110 then routes the transaction appropriately.

As discussed above, the transaction data itself may include line-level information for substantiating transactions as eligible medical expenses and automating the reimbursement process. The transaction data may also include detailed transaction information for determining whether each product and/or service is eligible for reimbursement (e.g., by including data elements derived from HAS database 108).

Upon receipt of the authorization request, the financial institution 102 or other acquirer may make an authorization decision via, for example, any credit authorization system or decision engine known in the art.

Typically, the financial institution 103 or acquirer will generate an "approval" authorization response if the credit line available on the credit account is equal to or exceeds the full dollar amount of the purchase. The financial institution 103 (e.g., via a credit authorization system) returns an authorization response 111 to the merchant's POS 105. This may be accomplished by transmitting the authorization response 111 to an authorization response router 112. The authorization response router 112 may be the same or different from the authorization router 110. In one embodiment, the authorization response router 112 is deployed in the financial institution 102's infrastructure, in another embodiment, authorization response router 112 is deployed in a transaction, payment, or association network.

The POS 105 receives the authorization response 111 from the authorization response router 112. If the transaction is approved, the POS 105 may generate a receipt for the user 101 via a receipt generation component. The receipt, for example, may distinguish or otherwise itemize qualified items identified by eligibility module 107 from data in HAS database 108. POS 105 may also include an imaging component for imaging the receipt, and a storage component for storing the receipt in a data storage device (e.g., a memory). Alternatively, the imaging component and storage component may be deployed at another location accessible by a network.

System 100 may also include a reimbursement engine 120. The reimbursement engine 120 may be deployed in the financial institution's infrastructure or elsewhere. The reimbursement engine 120 leverages data received from the merchant POS (e.g., transaction data, line item data, BIN data, data identifying qualifying products, etc.) and user 101 defined enrollment criteria (e.g., reimbursement preferences, etc.) to initiate a secondary transaction for "reimbursement" of the qualified healthcare purchases. In one example, reimbursement engine 120 transmits a reimbursement request 121 for the user's qualified purchase amount to the TPA 102 via a reimbursement request router 122. The reimbursement request 121 may include product or other purchase data, purchase price, user identification, or other line item data, and the total reimbursement amount requested. Reimbursement request router 122 may be, for example, a transaction or payment network, the ACH Network (a nationwide batch-oriented electronic funds transfer system) or an association network (e.g., Visa®), depending on the user defined enrollment criteria or the FSA debit account requirements. TPA 102 or other entity may receive the reimbursement request 121 and process the request via, for example, a reimbursement request processing engine 130.

The reimbursement request processing engine 130 may be deployed in TPA 102's infrastructure or elsewhere. The reimbursement request processing engine 130 may include an evaluation module including rules for evaluating product, line item, price, or other data from reimbursement request 121; an authorization determination module including rules for approving or declining reimbursement requests, and an authorization generation module for generating an authorization message. In one embodiment, the reimbursement request processing engine 130 accesses an intermediary database when processing the reimbursement request (e.g., a database including data regarding qualified purchases). For example, reimbursement request processing engine 130 may access a reimbursement database 131 to compare the data contained in reimbursement request 121 to corresponding qualified product data in reimbursement database 131, and provide commands to the authorization generation module to generate a reimbursement authorization response 140.

Once the authorization request 121 is processed, the authorization generation module of the authorization processing engine 130 may generate an reimbursement authorization response 140. The reimbursement authorization response 140 may include a reimbursement payment amount total or other data. Authorization processing engine 130 may then transmit reimbursement authorization response 140 to financial institution 103 via a reimbursement authorization response router 141. The reimbursement authorization response router 141 may be the same or different than reimbursement request router 122, and may be, for example, a transaction or payment network, an ACH Network, or an association network.

Financial institution 103 may receive and process reimbursement authorization response 140, by, for example, a reimbursement application engine 150. The financial institution may act as "an agent of" TPA 102 for processing reimbursement transactions. Reimbursement application engine 150 may apply the reimbursement payment amount total to the user 101's outstanding credit account balance, and/or record the reimbursement payment amount total on the customer's credit statement. For example, the reimbursement payment amount total may be applied toward the balance the user 101 owes the financial institution 103. Alternatively, the reimbursement application engine 150 may decline to apply a reimbursement payment amount total to the user 101's outstanding credit account balance due to, e.g., lack of funding in the qualified healthcare account. Thereafter, user 101 will be responsible to remit payment to the financial institution for balance remaining on the credit account, if any.

Single Transaction Model with Split

Figure 2:
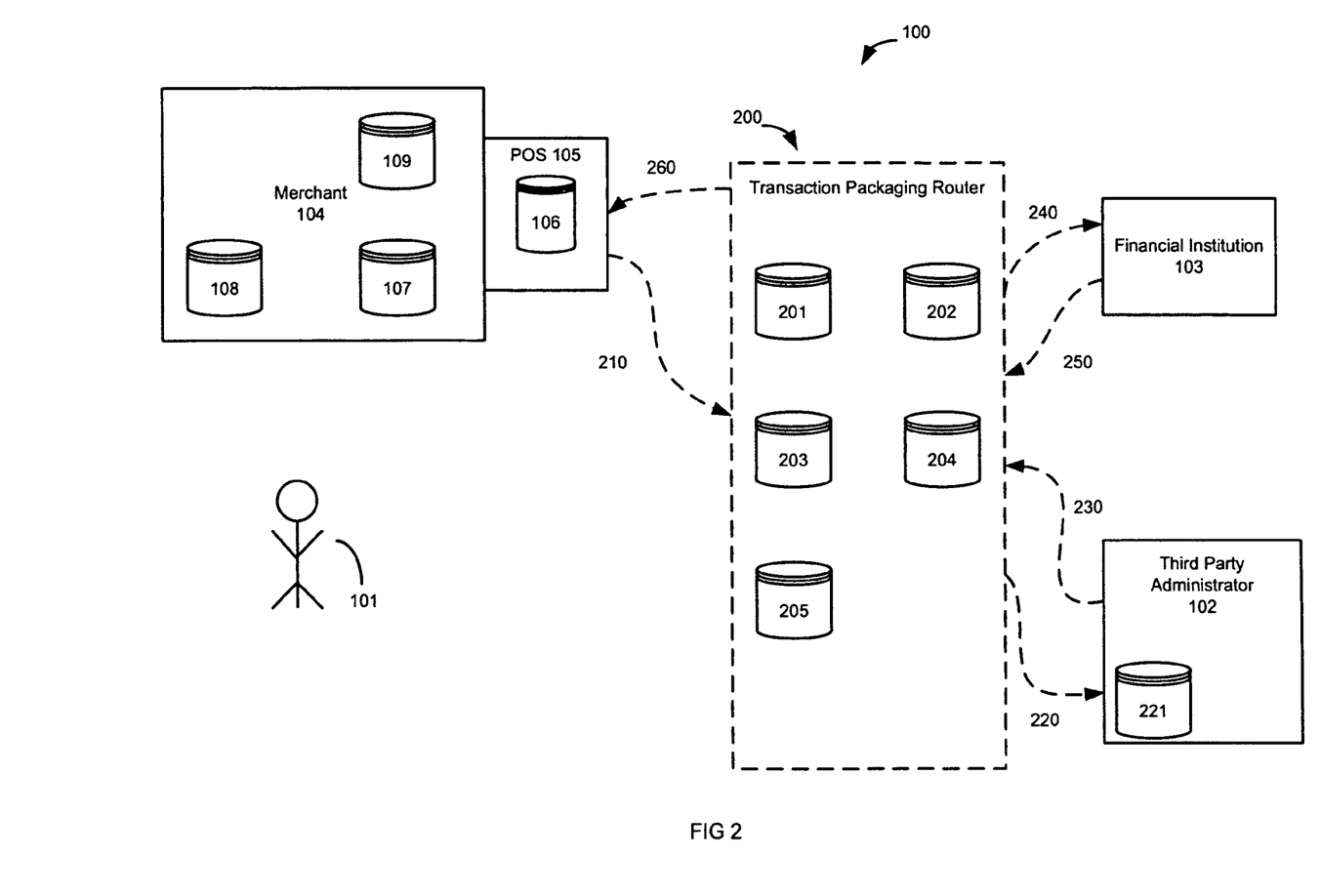
FIG. 2 is a block diagram of a system architecture suitable for implementing a single transaction model with split according to exemplary embodiments of the present invention.

According to an exemplary single transaction model with split of another embodiment of the system 100 of the present invention, POS processor 106 processes an authorization credit transaction for the full dollar amount of the user 101's purchase. As discussed above, the transaction data itself may include line-level information for substantiating transactions as eligible medical expenses and automating the reimbursement process.

The transaction data may also include detailed transaction information for determining whether each product and/or service is eligible for reimbursement (e.g., by including data elements derived from HAS database 108. For example, the transaction information may include type of product or service, price, purpose, product or service code, date/time of purchase, credit card account data, FSA account data, merchant data, etc. In one embodiment, POS 105 generates an authorization request and transaction data 210 and transmits the authorization request 210 to transaction packaging router 200. Transaction packaging router 200 may be, for example, a transaction, payment, association, or other network.

Transaction packaging router 200 may include routing rules engine 201, customer defined criteria rules engine 202, PAN cross-reference engine 203, re-packaging engine 204, and authorization response evaluation engine 205. Each of routing rules engine 201, customer defined criteria rules engine 202, PAN cross-reference engine 203, re-packaging engine 204, and authorization response evaluation engine 205 may access intermediary databases (not shown) when processing a customer's transaction (to obtain, for example, BIN files, product information, data about a purchase, etc.).

In one example, transaction packaging router 200 receives the authorization request and transaction data 210. Routing rules engine 201 matches the user's credit card's BIN data contained in the authorization request 210 to corresponding BINs in a BIN file to identify that the purchase relates to a credit account linked to an FSA debit account. The user's credit card's BIN may be also associated with specific routing instructions in routing rules engine 201. In an alternative embodiment, the POS terminal 105 includes an identification module for matching the credit card's BIN to a corresponding BIN in POS BIN file 109 and transmits identification data to transaction packaging router 200 to enable transaction packaging router 200 to recognize that the authorization request relates to a linked credit account and FSA debit account.

Upon recognition that the user's purchase relates to a linked credit account and FSA debit account, transaction packaging router 200 thereafter differentiates the portion of the transaction representing the qualified healthcare items purchase from the portion of the transaction representing non-qualified items. The portion of the transaction representing qualified healthcare items may be differentiated by evaluating the line-level information transmitted in the authorization request for substantiating transactions as eligible medical expenses.

The transaction packaging router 200 then applies routing rules via routing rules engine 201 and/or customer defined criteria engine 202, and routes the authorization request. For example, customer defined criteria engine 202 may access an intermediary database that includes data representing the user's enrollment criteria, to determine, for example, the user's pre-defined healthcare "end-point," e.g., TPA 102.

The transaction packaging router 200 may then "package" the portion of the authorization request and transaction data representing qualified healthcare items purchase for routing to TPA 102 or other end-point via re-packaging engine 204. For example, transaction packaging router 200 may package the authorization request and transaction data to include only the total payment amount associated with the auto-substantiated qualified healthcare purchases and product data. In another embodiment, PAN cross-reference engine 203 may also replace the credit card related data in the authorization request with FSA debit account related data. Transaction packaging engine router 200 then routes the authorization request to TPA or other end-point for authorization 220 to debit the FSA debit account for the total payment amount associated with the qualified healthcare purchases.

TPA 102 or other end-point receives the packaged authorization request 220 representing qualified healthcare items. TPA 102 may have an authorization request processing engine 221 deployed in TPA 102's infrastructure. The authorization request processing engine 221 may include an evaluation module including rules for evaluating product, line item, price, or other data from authorization request 220; an authorization determination module including rules for approving or declining authorization requests, and an authorization generation module for generating an authorization message. In one embodiment, the authorization request processing engine 221 accesses an intermediary database when processing the reimbursement request (e.g., a database including data regarding qualified, reimbursable goods and services). For example, authorization request processing engine 221 may access a reimbursement database to compare the data contained in authorization request 220 to corresponding qualified product data in the reimbursement database, and provide commands to the authorization generation module to generate an authorization response 230.

Once the authorization request 220 is processed, the authorization generation module of the authorization request processing engine 221 may generate an authorization response 230. The authorization response 230 may include a payment amount total or other data. Authorization request processing engine 221 may then transmit authorization response 230 back to the transaction processing router 200.

The transaction processing router 200 receives the authorization response 230, and may evaluate it with authorization response evaluation engine 205. For example, authorization response evaluation engine 205 may subtract the payment amount authorized by TPA 102 from the total transaction purchase amount. Re-packaging engine 204 may then generate an authorization request 240 including any remaining transaction purchase amount (representing the purchase of any non-qualified items) for routing to financial institution 103 for credit transaction authorization. Transaction processing and packaging router 200 routes the authorization request 240 to the financial institution 103.

Upon receipt of the authorization request, the financial institution 102 or acquirer may make an authorization decision via, for example, any credit authorization system or decision engine known in the art.

Typically, the financial institution 103 or acquirer will generate an "approval" authorization response if the credit line available on the credit account is equal to or exceeds the full dollar amount of the purchase. The financial institution 103 (e.g., via a credit authorization system) returns an authorization response 250 to the transaction packaging router 200.

Transaction packaging router 200 receives the authorization response 250 from financial institution 103. Re-packaging engine 204 of transaction packaging router 200 then "re-packages" the authorization responses 230 and 250 from both the TPA 102 and financial institution 103 into a single authorization response 160. Transaction packaging router 200 then transmits the single authorization response 160 back to the merchant's POS terminal 105. The merchant thereafter completes the transaction as discussed above.

Two Transaction Model

Figure 3:
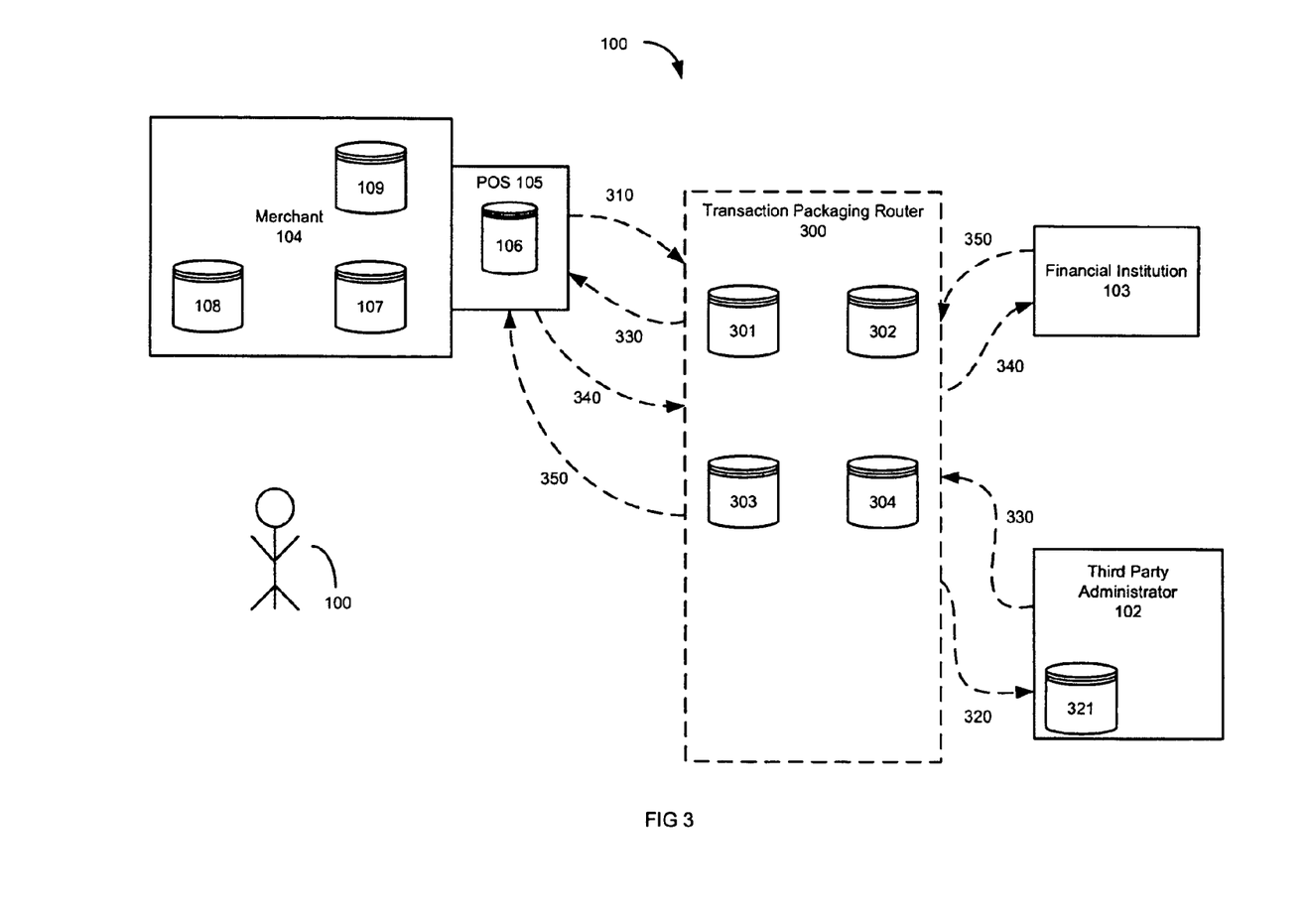
FIG. 3 is a block diagram of a system architecture suitable for implementing a two transaction model according to exemplary embodiments of the present invention; and The examples set out herein illustrate several embodiments of the invention but should not be construed as limiting the scope of the invention in any manner. Corresponding reference characters indicate corresponding parts throughout the several views.

According to an exemplary two transaction model of another embodiment of the system 100 of the present invention, POS processor 106 processes an authorization credit transaction for the full dollar amount of the user 101's purchase. As discussed above, the transaction data itself may include line-item information for substantiating transactions as eligible medical expenses and automating the reimbursement process.

The transaction data may also include detailed transaction information for determining whether each product and/or service is eligible for reimbursement (e.g., by including data elements derived from IIAS database 108. For example, the information may include type of product or service, price, purpose, product or service code, date/time of purchase, credit card account data, FSA account data, merchant data, etc. In this embodiment, POS 105 generates an authorization request and transaction data 310 and transmits the authorization request 310 to transaction packaging router 300. Transaction packaging router 300 may be, for example, a transaction, payment, association, or other network.

Transaction packaging router 300 may include software including routing rules engine 301, customer defined criteria rules engine 302, PAN cross-reference engine 303, and re-packaging engine 304. Each of routing rules engine 301, customer defined criteria rules engine 302, PAN cross-reference engine 303, and re-packaging engine 304 may access intermediary databases (not shown) when processing a customer's transaction (to obtain, for example, BIN files, product information, data about a purchase, etc.).

In one example, transaction packaging router 300 receives the authorization request and transaction data 310. Routing rules engine 301 matches the user's credit card's BIN contained in the authorization request 310 to corresponding BINs in a BIN file to identify that the purchase relates to a linked credit account and FSA debit account. The user's credit card's BIN may be also associated with specific routing instructions in routing rules engine 301. In an alternative embodiment, the POS terminal 105 includes an identification module for matching the credit card's BIN to a corresponding BIN in POS BIN file 109 and transmits identification data to transaction packaging router 300 to enable transaction packaging router 300 to recognize that the authorization request relates to a linked credit account and consumer healthcare debit account.

Upon recognition that the user's purchase relates to a linked credit account and consumer healthcare account, e.g., an FSA debit account, transaction packaging router 200 thereafter differentiates the portion of the transaction representing qualified healthcare items purchase from the portion of the transaction representing non-qualified items. The portion of the transaction representing qualified healthcare items may be differentiated by evaluating the line-level information transmitted in the authorization request.

The transaction packaging router 300 then applies routing rules via routing rules engine 301 and/or customer defined criteria engine 302, and routes the authorization request. For example, customer defined criteria engine 302 may access an intermediary database that includes data representing the user's enrollment criteria, to determine, for example, the user's pre-defined healthcare "end-point," e.g., TPA 102.

The transaction packaging router 300 may then "package" the portion of the authorization request and transaction data representing qualified healthcare items purchase for routing to TPA 102 or other end-point via re-packaging engine 304. For example, transaction packaging router 300 may package the authorization request and transaction data to include only the total payment amount associated with the healthcare purchases and product data. In another embodiment, PAN cross-reference engine 303 may also replace the credit card related data in the authorization request with FSA debit account related data. Transaction packaging engine router 300 then routes the authorization request to TPA for authorization 320 to debit the FSA debit account for the total payment amount associated with the qualified healthcare purchases.

TPA 102 or other end-point receives the packaged authorization request 220 representing qualified healthcare items. TPA 102 may have an authorization request processing engine 321 deployed in TPA 102's infrastructure. The authorization request processing engine 321 may include an evaluation module including rules for evaluating product, line item, price, or other data from authorization request 320; an authorization determination module including rules for approving or declining authorization requests, and an authorization generation module for generating an authorization message. In one embodiment, the authorization request processing engine 321 accesses an intermediary database when processing the reimbursement request (e.g., a database including data regarding qualified, reimbursable goods and services). For example, authorization request processing engine 321 may access a reimbursement database to compare the data contained in authorization request 320 to corresponding qualified product data in the reimbursement database, and provide commands to the authorization generation module to generate an authorization response 330.

Once the authorization request 320 is processed, the authorization generation module of the authorization request processing engine 321 may generate an authorization response 330. The authorization response 330 may include an authorized payment amount total or other data. Authorization request processing engine 321 may then transmit authorization response 330 back to the transaction processing router 300.

The transaction processing router 300 retrieves the authorization response 330. The transaction processing router 300 then routes the authorization response 330 to the merchant's POS terminal 105. The merchant may then either: (1) generate a subsequent authorization request 340 via POS terminal 105 and transmit the subsequent authorization response 340 to the transaction packaging router 300 directed to the financial institution 103 for the remaining purchase balance (e.g., by automatically using terminal logic (BIN) to recognize multi-purse characteristics); or (2) manually prompt the user 101 for another form of payment.

If the former, the transaction packaging router 200 receives the subsequent authorization request 340 and transmits the subsequent authorization request 340 directly to the financial institution 103 or other acquirer for approval.

As discussed above, financial institution 103 may process the authorization request 340 and return an authorization response 350 to the transaction packaging router 300 for the remaining portion of the purchase. Upon receipt of the authorization request, the financial institution 103 or acquirer may make an authorization decision via, for example, any credit authorization system or decision engine known in the art. Typically, the financial institution 103 or acquirer will generate an "approval" authorization response if the credit line available on the credit account is equal to or exceeds the full dollar amount of the purchase. The transaction packaging router 300 thereafter transmits the authorization response 350 to the merchant. The merchant thereafter completes the transaction as discussed earlier.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

We claim:

1. A computer implemented method for processing consumer healthcare account related reimbursement eligible transactions, the computer implemented method comprising:
   issuing a user a credit card payment device associated with a credit account and a consumer healthcare account, the credit card payment device effecting payment from a first payment source for purchases eligible for reimbursement by the consumer healthcare account pursuant to one or more transaction rules governing the eligibility for reimbursement of purchases made by consumer healthcare accounts, and effecting payment from a second payment source for purchases not eligible for reimbursement by the consumer healthcare account, wherein said transaction rules determine the reimbursement eligibility of the purchases;
   identifying a user transaction made with the payment device at a merchant for one or more purchases;
   receiving merchant data regarding the user transaction including an authorization request;
   determining, using a computer processor, whether the user transaction is authorized and transmitting a response to the authorization request; and
   debiting the user from the second payment source if the transaction is unauthorized, and performing reimbursement steps if the transaction is authorized, and if at least a portion of the transaction is eligible for reimbursement, the reimbursement steps including:
      identifying, using a reimbursement engine including computer processing components, reimbursable expenses in the transaction based at least in part on the merchant data;
      transmitting a reimbursement request using the computer processing components to a consumer healthcare account administrator for reimbursable expenses;
      receiving a reimbursement request response at the reimbursement engine from the consumer healthcare account administrator; and
      reimbursing the user for reimbursable expenses implementing computer processing components of a reimbursement application engine based at least in part on the reimbursement request response from the consumer healthcare account administrator.

2. The method of claim 1, wherein the merchant data regarding the user transaction including an authorization request is received from a transaction, payment, or association network.

3. The method of claim 1, wherein the merchant data regarding the user transaction includes line-item product data.

4. The method of claim 1, wherein the merchant data regarding the user transaction identifies reimbursable expenses.

5. The method of claim 1, wherein the merchant data regarding the user transaction is derived at least in part from an inventory information approval system.

6. The method of claim 1, wherein the merchant data regarding the user transaction includes the full dollar amount of the transaction.

7. The method of claim 1, wherein the user transaction is identified at least in part by evaluating a payment device bin identification number or issuer identification number.

8. The method of claim 1, wherein the reimbursement request is transmitted from the reimbursement engine to a flexible spending account administrator.

9. The method of claim 1, wherein the reimbursement request response is received from a flexible spending account administrator.

10. The method of claim 1 further comprising: generating a credit account statement identifying reimbursed expenses.

11. The method of claim 1, wherein the credit account is associated with a rewards program.

12. The method of claim 1, wherein the first payment source and the second payment source are combined into a single account.

13. The method of claim 1, wherein the first payment source and the second payment source are separate accounts.

14. A computer implemented method for processing consumer healthcare account related reimbursement eligible transactions, the computer implemented method comprising:
   identifying a user transaction initiated at a merchant for one or more purchases made with a credit card payment device associated with a credit account and a consumer healthcare account, the credit card payment device effecting payment from a first payment source for purchases eligible for reimbursement by the consumer healthcare account pursuant to one or more transaction rules governing the eligibility for reimbursement of purchases made by consumer healthcare accounts, and effecting payment from a second payment source for purchases not eligible for reimbursement by the consumer healthcare account, wherein said transaction rules determine the reimbursement eligibility of the purchases;
   receiving merchant data regarding the user transaction including an authorization request;
   differentiating, based on the received merchant data, using computer processing components of a transaction packaging router, reimbursable expenses from non-reimbursable expenses in the user transaction;
   transmitting, using the computer processing components of the transaction packaging router, an authorization request to a consumer healthcare account administrator, wherein the authorization request includes at least some merchant data for identifying the reimbursable expenses in the transaction;

receiving a response to the authorization request from the consumer healthcare account administrator;

transmitting, using the computer processing components of the transaction packaging router, an authorization request to a credit account issuer including at least some merchant data identifying the non-reimbursable expenses in the transaction;

receiving a response to the authorization request from the credit account issuer; and transmitting, using the computer processing components of the transaction packaging router, an authorization response to the merchant including at least in part the response to the authorization request from the consumer healthcare account administrator and the response to the authorization request from the credit account issuer.

15. The method of claim 14, wherein the merchant data regarding the user transaction is received from a transaction, payment, or association network.

16. The method of claim 14, wherein the merchant data regarding the user transaction includes line-item product data.

17. The method of claim 14, wherein the merchant data regarding the user transaction identifies reimbursable expenses.

18. The method of claim 14, wherein the merchant data regarding the user transaction is derived at least in part from an inventory information approval system.

19. The method of claim 14, wherein the merchant data regarding the user transaction includes the full dollar amount of the transaction.

20. The method of claim 14, wherein the first payment source and the second payment source are combined into a single account.

21. The method of claim 14, wherein the first payment source and the second payment source are separate accounts.

22. A computer implemented method for processing consumer healthcare account related reimbursement eligible transactions, the computer implemented method comprising:

identifying a user transaction initiated at a merchant for one or more purchases made with a credit card payment device, the credit card payment device effecting payment from a first payment source for purchases eligible for reimbursement by the consumer healthcare account pursuant to one or more transaction rules governing the eligibility for reimbursement of purchases made by consumer healthcare accounts, and effecting payment from a second payment source for purchases not eligible for reimbursement by the consumer healthcare account, wherein said transaction rules determine the reimbursement eligibility of the purchases;

receiving merchant data regarding the user transaction including an authorization request;

determining, using computer processing components of a transaction packaging router, that the payment device is linked to the credit account and a consumer healthcare debit account;

transmitting, using the computer processing components of the transaction packaging router, an authorization request to a consumer healthcare account administrator, wherein the authorization request includes at least some merchant data for identifying reimbursable expenses in the transaction;

receiving an authorization response from the consumer healthcare account administrator;

transmitting, using the computer processing components of the transaction packaging router, the authorization response to the merchant including at least in part the response to the authorization request from the consumer healthcare account administrator;

receiving merchant data regarding the user transaction including a second authorization request;

transmitting, using the computer processing components of the transaction packaging router, merchant data including the second authorization request to a credit account issuer;

receiving a response to the second authorization request from the credit account issuer; and transmitting an authorization response to the merchant including at least in part the response to the authorization request from the credit account issuer.

23. The method of claim 22, wherein the merchant data regarding the user transaction is received from a transaction, payment, or association network.

24. The method of claim 22, wherein the merchant data regarding the user transaction includes line-item product data.

25. The method of claim 22, wherein the merchant data regarding the user transaction identifies reimbursable expenses.

26. The method of claim 22, wherein the merchant data regarding the user transaction is derived at least in part from an inventory information approval system.

27. The method of claim 22, wherein the merchant data regarding the user transaction includes the full dollar amount of the transaction.

28. The method of claim 22, wherein the first payment source and the second payment source are combined into a single account.

29. The method of claim 22, wherein the first payment source and the second payment source are separate accounts.

30. A system for processing consumer healthcare account related reimbursement eligible transactions, the system comprising:

a processor for processing a credit transaction for a purchase made with a credit card payment device associated with a credit account and a consumer healthcare account, the credit card payment device effecting payment from a first payment source for purchases eligible for reimbursement by the consumer healthcare account pursuant to one or more transaction rules governing the eligibility for reimbursement of purchases made by consumer healthcare accounts, and effecting payment from a second payment source for purchases not eligible for reimbursement by the consumer healthcare account, wherein said transaction rules determine the reimbursement eligibility of the purchases;

an eligibility module implementing computer processing components for identifying consumer healthcare account reimbursement eligible expenses in the purchase;

an authorization request router for routing authorization requests from a requestor to a financial institution;

a credit authorization decision engine implementing computer processing components for decisioning on authorization requests and generating authorization responses;

an authorization response router for routing authorization responses to the requestor from the financial institution;

a reimbursement engine implementing computer processing components for leveraging data received from the authorization request router to initiate a transaction for reimbursement of eligible expenses in the purchase; and a reimbursement application engine implementing computer processing components for applying reimbursement payment amount data.

31. The system of claim 30, wherein the reimbursement engine is operable to generate a reimbursement request.

32. The system of claim 31, further comprising a reimbursement request processing engine for processing a reimbursement request.

33. The system of claim 32, wherein the reimbursement request processing engine includes an authorization generation module for generating an authorization response, wherein the authorization response includes at least a reimbursement payment amount.

34. The system of claim 33 wherein the authorization processing engine is further operable to transmit the reimbursement authorization response via a reimbursement authorization response router.

35. The system of claim 32, wherein the reimbursement request processing engine includes one or more of: an evaluation module including rules for evaluating product, line item, price, or other data from a reimbursement request; an authorization determination module including rules for approving or declining reimbursement requests; and an authorization generation module for generating an authorization response.

36. The system of claim 31, wherein the reimbursement request includes at least one of: product data, purchase data, purchase price, user identification, line item data, and the total reimbursement amount requested.

37. The system of claim 31, further comprising a reimbursement request router.

38. The system of claim 30, wherein the eligibility module is operable to access an inventory information approval system.

39. The system of claim 38, wherein the eligibility module is operable to access product and/or service data, including: line-item data, price data, product purpose data, product code data, service code data, date of purchase data, time of purchase data, and merchant identification data.

40. The system of claim 30, wherein the authorization request router is a transaction, payment, or association network.

41. The system of claim 30, further comprising an identification module for matching a bin identification number associated with the payment device to a corresponding bin identification number in a bin identification number file.

42. The method of claim 30, wherein the first payment source and the second payment source are combined into a single account.

43. The method of claim 30, wherein the first payment source and the second payment source are separate accounts.

44. A system for processing consumer healthcare account related reimbursement eligible transactions, the system comprising:
 a processor for processing a credit transaction for a purchase with a credit card payment device associated with a credit account and a consumer healthcare account, the credit card payment device effecting payment from a first payment source for purchases eligible for reimbursement by the consumer healthcare account pursuant to one or more transaction rules governing the eligibility for reimbursement of purchases made by consumer healthcare accounts, and effecting payment from a second payment source for purchases not eligible for reimbursement by the consumer healthcare account, wherein said transaction rules determine the reimbursement eligibility of the purchases;
 a transaction packaging router for routing authorization requests;
 a routing rules engine implementing computer processing components for at least one of identifying the purchase with a payment device associated with a credit account and a consumer healthcare account and applying routing rules;
 a customer defined criteria rules engine implementing computer processing components for creating routing rules dependent at least in part upon the user's consumer healthcare account enrollment criteria; and
 a credit authorization decision engine implementing computer processing components for decisioning on authorization requests and generating authorization responses.

45. The system of claim 44, further comprising an eligibility module for identifying consumer healthcare account reimbursement eligible expenses in the user's purchase.

46. The system of claim 45, wherein the user's transaction data is accessible by a user for one or more of review, modification, and download.

47. The system of claim 44, wherein the transaction packaging router is operable to differentiate consumer healthcare account reimbursable expenses from other expenses in the transaction.

48. The system of claim 44, further comprising a primary account number cross-reference engine for substituting credit card related data in an authorization request with consumer healthcare account related data.

49. The system of claim 44, wherein the transaction packaging router is part of a transaction, payment, or association network.

50. The system of claim 44, further comprising an authorization request processing engine for processing an authorization request.

51. The system of claim 44, further comprising an authorization response generation module for generating an authorization response.

52. The system of claim 44, further comprising an evaluation module including rules for evaluating product, line item, price, or other data from an authorization request.

53. The system of claim 44, further comprising a storage module for storing a user's transaction data.

54. The system of claim 44, further comprising a re-packaging engine for generating packaged authorization requests.

55. The system of claim 44, further comprising an authorization response evaluation engine for evaluating authorization responses.

56. The method of claim 44, wherein the first payment source and the second payment source are combined into a single account.

57. The method of claim 44, wherein the first payment source and the second payment source are separate accounts.

58. A system for processing consumer healthcare account related reimbursement eligible transactions, the system comprising:
 a processor for processing a credit transaction for a purchase made with a credit card payment device associated with a credit account and a consumer healthcare account, the credit card payment device effecting payment from a first payment source for purchases eligible for reimbursement by the consumer healthcare account pursuant to one or more transaction rules governing the eligibility for reimbursement of purchases made by consumer healthcare accounts, and effecting payment from a second payment source for purchases not eligible for reimbursement by the consumer healthcare account, wherein said transaction rules determine the reimbursement eligibility of the purchases;

an identification module for matching a bin identification number associated with the payment device to a corresponding bin identification number in a bin identification number file;

an eligibility module implementing computer processing components for identifying consumer healthcare account reimbursement eligible expenses in the purchase, wherein the eligibility module is operable to access an inventory information approval system to access product and/or service data, including: line-item data, price data, product purpose data, product code data, service code data, date of purchase data, time of purchase data, and merchant identification data;

a reimbursement engine implementing computer processing components for leveraging data received from the authorization request router to initiate a transaction for reimbursement of eligible expenses in the purchase, wherein the reimbursement engine is operable to generate a reimbursement request, the reimbursement request includes at least one of: product data, purchase data, purchase price, user identification, line item data, and the total reimbursement amount requested;

a reimbursement request router;

a reimbursement request processing engine for processing a reimbursement request, wherein the reimbursement request processing engine includes an authorization generation module for generating an authorization response, wherein the authorization response includes at least a reimbursement payment amount;

an authorization request router for routing authorization requests from a requestor to a financial institution, wherein the authorization request router is a transaction, payment, or association network;

a credit authorization decision engine implementing computer processing components for decisioning on authorization requests and generating authorization responses;

an authorization response router for routing authorization responses to the requestor from the financial institution; and a reimbursement application engine implementing computer processing components for applying reimbursement payment amount data.

\* \* \* \* \*